United States Patent [19]

Glenn

[11] Patent Number: 5,209,225
[45] Date of Patent: May 11, 1993

[54] FLOW THROUGH NEBULIZER

[76] Inventor: Joseph G. Glenn, Box 91, Broken Arrow, Okla. 74013

[21] Appl. No.: 794,252

[22] Filed: Nov. 19, 1991

[51] Int. Cl.[5] .............................................. A61M 11/00
[52] U.S. Cl. ........................... 128/200.14; 128/200.18; 128/200.21; 128/203.12; 239/338; 261/DIG. 65
[58] Field of Search ....................... 128/200.11, 200.12, 128/200.13, 200.14, 200.16, 200.18, 200.19, 200.21, 200.22, 200.23, 203.12, 203.25; 261/78.2, 16, DIG. 65; 239/338, 343, 370, 390, 396

[56] References Cited

U.S. PATENT DOCUMENTS

| | | |
|---|---|---|
| 2,826,454 | 3/1958 | Coanda . |
| 3,158,154 | 11/1964 | Schreiber ........................ 128/203.25 |
| 3,561,444 | 2/1971 | Boucher ................... 261/DIG. 65 X |
| 3,658,059 | 4/1972 | Steil .................................. 128/200.21 |
| 4,007,238 | 2/1977 | Glenn ........................ 261/DIG. 65 |
| 4,116,387 | 9/1978 | Kremer, Jr. et al. . |
| 4,251,033 | 2/1981 | Rich et al. ................... 128/200.21 X |
| 4,301,970 | 11/1981 | Craighero ................... 128/200.17 X |
| 4,512,341 | 2/1985 | Lester . |
| 4,566,451 | 1/1986 | Badewien . |
| 4,657,007 | 4/1987 | Carlin et al. ................ 128/200.18 X |
| 4,746,067 | 5/1988 | Svoboda ..................... 128/200.18 X |
| 4,792,097 | 12/1988 | Kremer et al. .............. 128/200.18 X |
| 5,054,477 | 10/1991 | Terada et al. .............. 128/200.22 X |

FOREIGN PATENT DOCUMENTS

| | | | |
|---|---|---|---|
| 8601731 | 3/1986 | European Pat. Off. ........ 128/200.21 |
| 1198298 | 8/1965 | Fed. Rep. of Germany . |
| 458268 | 7/1950 | Italy ................................. 128/203.25 |

Primary Examiner—William H. Grieb
Assistant Examiner—Sebastiano Passaniti
Attorney, Agent, or Firm—Head & Johnson

[57] ABSTRACT

A nebulizer having a bottom cup for storing liquid medication. The bottom cup has an opening therethrough to receive a source of pressurized air. A housing includes an open bottom removably attachable to the bottom cup, an open top outlet, walls extending therebetween, and an air inlet tube extending through one of the walls, traversing the housing, and terminating in an aperture adjacent the open bottom so that air entering the inlet tube will pass through and across the housing before entering the housing adjacent the open bottom. A cover is receivable within the bottom cup so that liquid medication can be drawn from the bottom cup by induction and form droplets, whereby the pressurized air and the liquid droplets will impinge on the air inlet tube of the housing, thereby breaking into micron-size droplets.

10 Claims, 4 Drawing Sheets

FLOW THROUGH NEBULIZER

BACKGROUND OF THE INVENTION

1. Field of the Invention

The present invention relates to a breathing device for administering a liquid medicant to a patient. In particular, the present invention is directed to a breathing device that is simple in design, easy to manufacture, and is comprised of a relatively small number of components.

2. Prior Art

The use of nebulizers or atomizers with intermittent positive pressure breathing (IPPB) equipment, ventilators, or with the patient's own natural breathing effort is widely practiced. Nebulizers or atomizers are used to deliver liquid medicants for a wide variety of medical conditions.

There is increasing concern over treatment of contagious diseases, the concern being both for infection of other patients and for infection of medical personnel. For this reason, the use of disposable nebulizers which are discarded after a single patient's use has become popular. While many nebulizers are produced so that they may be washed and sterilized, and then reused, there is a demand for disposable nebulizers.

Although existing nebulizers may be discarded after each use, it is costly to discard the more expensive, complicated nebulizers.

Disposable nebulizers produced in the past have not been as effective as the reusable nebulizers. As an example, the Applicant's invention shown in U.S. Pat. No. 4,007,238 includes a feature not common to disposable nebulizers. The performance of the nebulizer is directly responsive to the patient's own breathing. Stated another way, the output of medication matches the patient's changing rate of inhalation. All of the air inhaled by the patient is directed past the saturated mist. As the air flow to the patient's lungs is increased, additional liquid particles are delivered to the lungs because these particles are surrounded by a shroud of high relative humidity. Conversely, when the air flow to the patient's lungs is decreased, the number of liquid particles is decreased. The amount of saturated air delivered to the patient is directly responsive to the increase or decrease in the patient's breathing.

Additionally, an extremely small average particle size is called for in delivery of liquid medication. For the liquid medication to reach the smaller passages in the bronchial tubes and lungs, the size of the liquid particles must be below five microns. These small particles are below the visible range.

Furthermore, the actual particle count delivered is of great importance.

It is desirable to incorporate these features in a nebulizer which is simple in design and is directed to the disposable market.

Accordingly, it is a principal object and purpose of the present invention to provide a nebulizer which is simple in construction, which is easy to produce, and which may be fabricated from a minimum number of components.

It is an additional object and purpose of the present invention to provide a disposable nebulizer having a medication delivery system that is responsive to the patient's breathing.

SUMMARY OF THE INVENTION

The nebulizer of the present invention includes a housing having a cylindrical chimney. At one end of the housing is an open bottom and at the opposite end, an open top outlet.

An atmospheric air inlet tube has a first end open. The air inlet tube extends through the cylindrical chimney and extends through and across the housing about the diameter of the chimney.

From its entry point, the air inlet tube extends to the opposite side of the chimney where a downward opening is provided. Ambient air entering the intake tube will, thus, travel through and across the housing and exit from the inlet tube toward the open bottom.

A bottom medication cup is removably attached to and encloses the open bottom of the housing. The bottom cup has a conical portion extending from a base. At the concentric top of the conical portion is an orifice. Extending from the conical portion, in communication with the orifice, is a nozzle holder which would be connected to a source of pressurized air.

Received within the bottom medication cup is a cover which nests on top of the conical portion of the bottom cup. The cover has an opening which is aligned with the orifice of the bottom cup.

A protruding target extends radially outward from the air intake tube. The protruding target extends outward toward the open bottom and toward the conical portion of the bottom cup. The protruding target is positioned so that it is above and spaced from the opening.

During operation of the nebulizer, a stream of pressurized air will flow through the orifice of the bottom cup causing induction of the liquid medication from the bottom cup through a space between the cup and the conical portion. Accordingly, liquid droplets of medication will be moved at high velocity into the housing.

The protruding target, thus, provides a target against which liquid droplets and pressurized air will move at high velocity. A stream of pressurized air and liquid droplets exiting from the opening will, thus, be caused to impinge against the target as well as against the air intake tube.

A pair of opposed, accurate skirts extend radially outward from the air intake tube and surround the protruding target.

Near the open bottom, the housing has an enlarged chamber axially aligned with the chimney, the housing having a larger diameter than the chimney. Air entering the air intake tube will pass across and through the housing within the intake tube, and will enter the enlarged chamber. Thereafter, the air will enter the chimney and pass around the horizontal air intake tube, mixing with the liquid droplets, vapor and pressurized air. Finally, the flow will-be directed upward through the interior of the chimney.

A longitudinal chamber extends adjacent the chimney in communication with the air intake tube. If the nebulizer is tipped from the upright position, the liquid medication will flow into the longitudinal chamber or the enlarged chamber. Thus, the liquid medication will not spill out of the open top or out of the air intake tube if the nebulizer is tipped from its upright position.

BRIEF DESCRIPTION OF THE DRAWINGS

FIG. 1 is a sectional view of a nebulizer constructed in accordance with the present invention;

FIG. 2 is a sectional view of an alternate embodiment of the present invention;

DETAILED DESCRIPTION OF THE PREFERRED EMBODIMENTS

Figure 1:
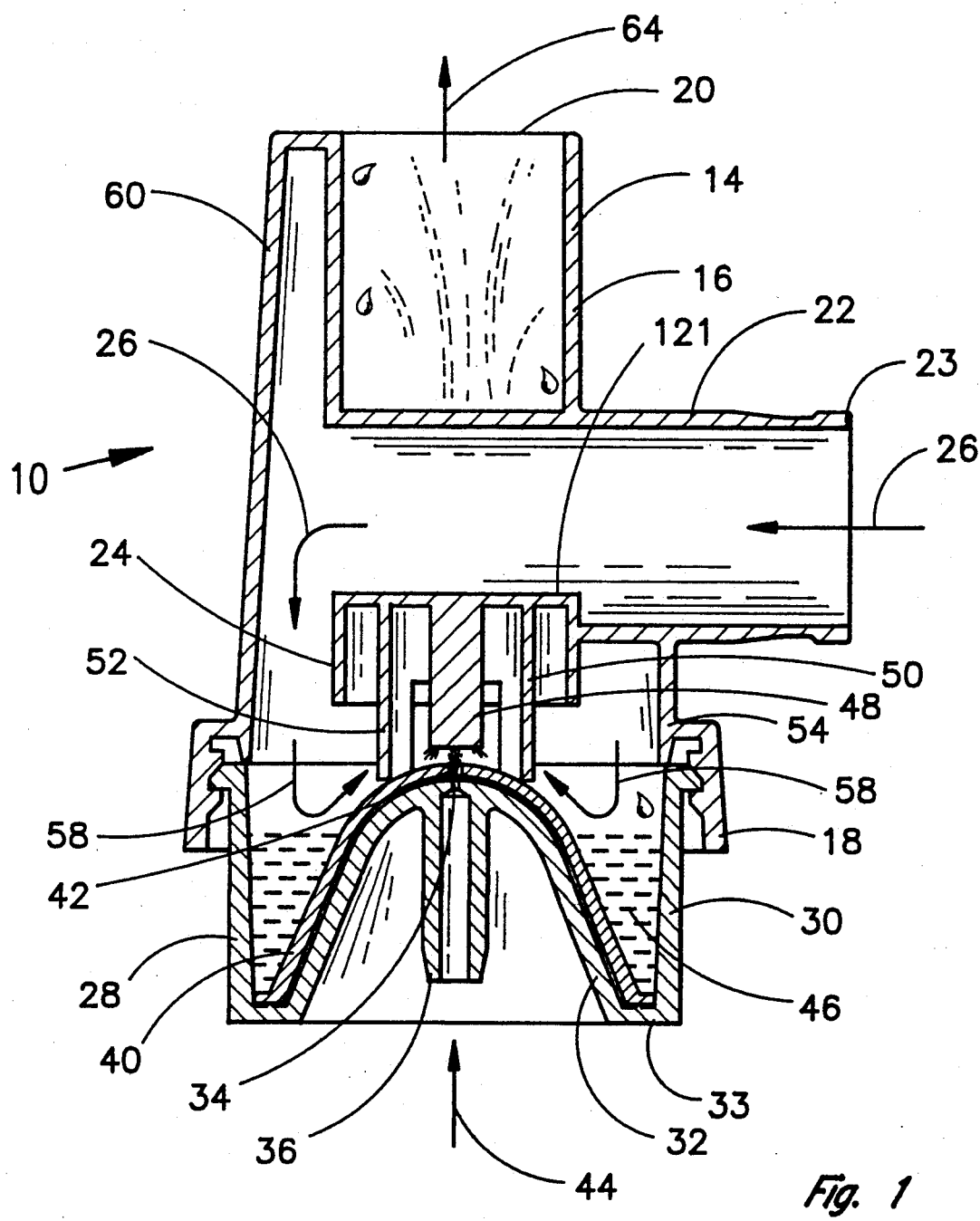

Referring to the drawings in detail, FIG. 1 illustrates a sectional view of a nebulizer 10 constructed in accordance with the present invention.

The nebulizer 10 includes a housing 14 which is normally positioned upright when in use. In the present embodiment, the housing 14 has substantially cylindrical walls to form a cylindrical chimney 16. At one end of the housing is an open bottom 18 and, at the opposite end, an open top outlet 20. It will be understood that although the chimney 16 is substantially cylindrical in the present embodiment, other shapes might also be utilized.

An atmospheric air inlet tube 22 has a first end 23 open. The air inlet tube 22 extends through the wall of the chimney 16 and extends through and across the housing 14, traversing the diameter of the chimney.

From its entry point, the air inlet tube extends to the opposite side of the chimney 16 where a downward opening 24 is provided. In the present embodiment, the air inlet tube is cylindrical in form and is substantially perpendicular to the cylindrical chimney 16 of the housing 14. Ambient air entering the air intake tube 22 will, thus, travel through and across the housing and exit from the tube 22 toward the open bottom 18 as shown by arrows 26.

A bottom medication cup 28 is removably attached to and encloses the open bottom 18 of the housing 14. In the embodiment shown, the open bottom 18 is internally threaded and the medication cup 28 is externally threaded. Other methods of attachment are, of course, possible. When the bottom cup 28 is attached, a closed chamber is formed, with the exception of the open end 23 of the air intake tube and the open top 20.

In the present embodiment, the bottom cup 28 has substantially cylindrical outer walls 30. The bottom cup 28 has a conical portion 32 extending from base 33 that is concentric with the walls 30. At the concentric top of the conical portion is an orifice 34. Extending from the conical portion and in communication with the orifice 34 is a nozzle holder 36. The nozzle holder 36 would be connected to a source of pressurized air (not shown) so that pressurized air would be delivered into the nebulizer.

Received within the bottom medication cup 28 is a cover 40 which nests on top of the conical portion 32 of the bottom cup 28. The cover 40 has an opening 42 which is aligned with the orifice 34 of the bottom cup.

During operation of the nebulizer 10, a stream of pressurized air indicated by arrow 44 will flow through the orifice 34 of the bottom cup and cause induction of the liquid medication 46 (illustrated by dashed lines) from the bottom cup through a space between the cover 40 and the conical portion 32. Accordingly, liquid droplets of medication will be moved at high velocity through the orifice and into the housing.

It will be recognized that other mechanisms to induct the liquid medication, such as a capillary tube, might alternatively be utilized.

Returning to a consideration of the housing 14, a protruding target 48 extends radially outward from the air intake tube 22. The protruding target 48 extends outward toward the open bottom 18 and the conical portion 32 of the bottom cup. The protruding target 48 is positioned so that it is above and spaced from the opening 42.

The protruding target 48, thus, provides a target against which liquid droplets and pressurized air will move at high velocity. The stream of pressurized air and liquid droplets exiting from the opening 42 will, thus, be caused to impinge against the target 48 and against the air intake tube 22. It will thus be observed that the air inlet tube itself serves as a baffling mechanism for the liquid particles.

A pair of opposed, accurate skirts 50 and 52 extend radially outward from the air intake tube 22 and surround the protruding target 48. The end of the skirts may touch and rest against the cover 40. Large droplets that remain after striking the target 48 and air intake tube will fall by gravity back into the medication cup. The liquid medication may then pass once again through the described system.

Near the open bottom 18, the housing has an enlarged chamber 54 axially aligned with the chimney and having a larger diameter than the chimney. Ambient air entering the air intake tube 22 will traverse the housing within the intake tube, and will enter the enlarged chamber 54. The air will then change direction and enter the chimney 16 as indicated by arrows 58. The air will pass around the horizontal air intake tube 22 and mix with the liquid droplets and pressurized air. The fine mist produced by the liquid droplets and pressurized air impinging on the target is mixed and swept along with the atmospheric air. The air flow will be directed upward through the interior of the chimney.

Finally, the saturated mist will exit the nebulizer 10 to be inhaled by the patient (not shown) from the top outlet 20 as indicated by the arrow 64.

Returning to a consideration of the air intake tube 22, a longitudinal chamber 60 extends adjacent the chimney 16. The chamber extends radially from and is in communication with the air intake tube. If the nebulizer 10 is accidentally tipped from the upright position, the liquid medication will flow into the chamber 60 if tipped in one direction or the enlarged chamber 54 if tipped in the opposite direction.

It will be observed that the entire nebulizer may be constructed of three component parts. The housing 14, including the air intake tube 22 and target 48 may be constructed of a single piece. The bottom medication cup 28 and the cover 40 comprise the only other components.

If a patient wishes to use a metered dose inhaler (MDI), the MDI can be added to the ambient air inlet tube 22 of the nebulizer 10. This permits the baffling system of the present invention to filter out the larger droplets of medication from the MDI. Use of the present invention with a metered dose inhaler will help overcome a systemic side effect of MDI's which is the ingestion of larger particles into the patient's stomach.

Distilled water might be placed in the medication cup while a MDI is being used. Flow from an air compressor or other pressurized air source generates a high relative humidity aerosol which blends with the medication.

Large droplets of medication would be filtered out an collected in the medication cup along with the distilled water. They would then be re-nebulized for delivery to the patient.

As seen in FIG. an additional check or flapper valve might be added to the nebulizer to further reduce the average particle size. The removable baffle mechanism might be inserted into the open top 20 of the housing. One type of check valve might be comprised of a flexible membrane which acts as a one way valve to allow the mist to exit from the chimney. As the patient inhales, the valve membrane would lift to allow the mist to pass from the chimney. The use of the valve membrane will also act as a secondary baffling system and restrict some of the larger particles from passing out of the open top.

By placing this additional mechanism in the chimney, large droplets will be knocked out and will descend, returning to the medication cup.

The present invention also is readily adaptable to presently existing filtration systems to prevent distribution of medication passing to the atmosphere. An inlet check valve or one way valve on the inlet side might easily be added to the open end 23 of the inlet tube 22. On the outlet side, a tee-connection with another one way check valve might be added. In this manner, the patient will inhale through the nebulizer as described herein. When the patient exhales, it will vent through the opposite side of the tee.

Figure 2:
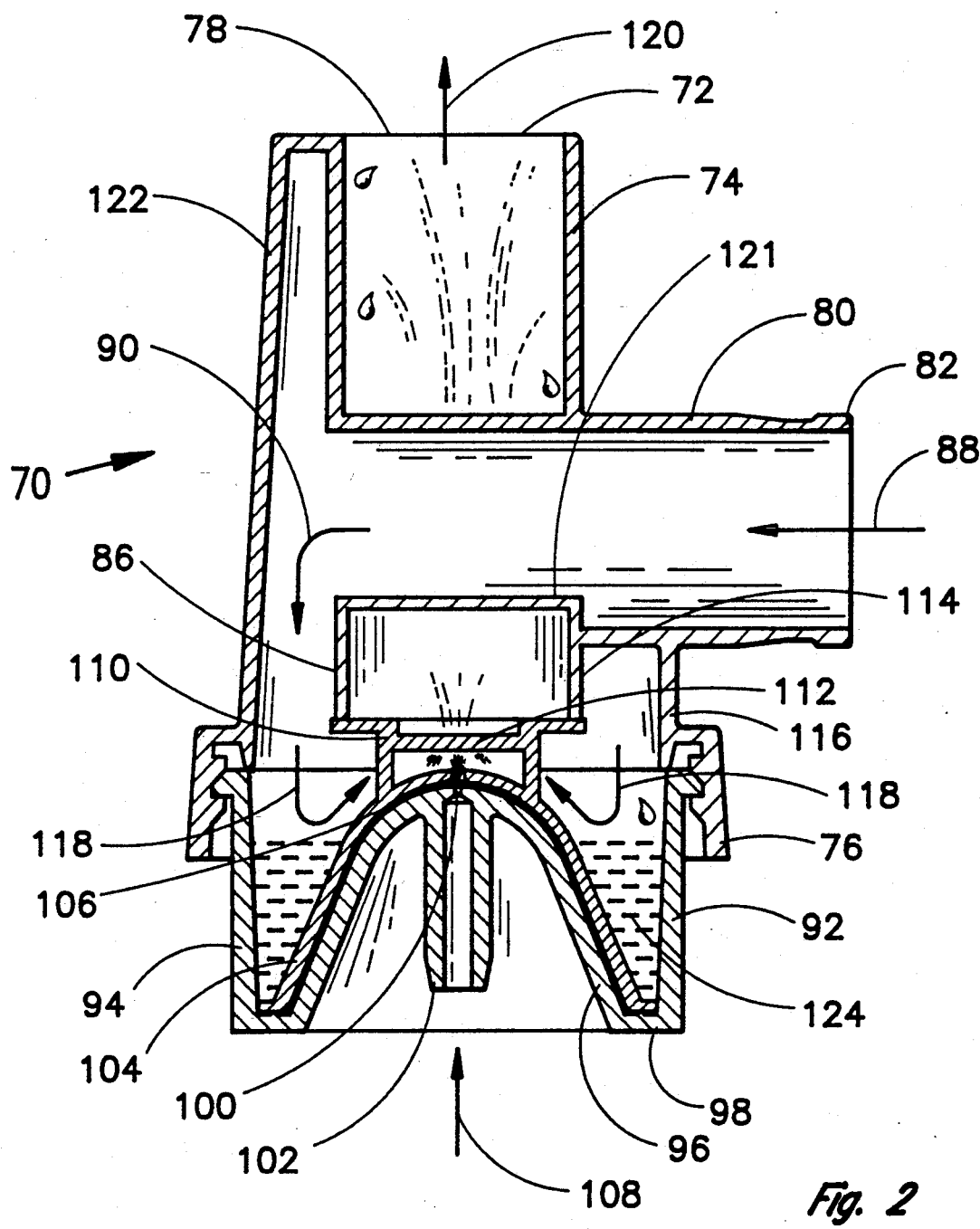

FIG. 2 illustrates an alternate embodiment 70 of the present invention. A housing 72 is normally positioned upright when the nebulizer is in use. The housing has a substantially cylindrical chimney 74. At one end of the housing is an open bottom 76 and, at the opposite end, an open top outlet 78.

An atmospheric air inlet tube 80 has a first end 82 which is open. The air inlet tube 80 extends through the wall of the chimney 74 and extends through and across the housing 72, traversing the diameter of the chimney 74.

From its entry point, the air inlet tube 80 extends to the opposite side of the chimney 74 where a downward opening 86 is provided. The air inlet tube is substantially perpendicular to the chimney of the housing 72. Ambient air entering the air intake tube will, thus, travel through and across the housing and exit from the tube toward the open bottom 76 as indicated by arrows 88 and 90.

A bottom medication cup 92 is removably attached to and encloses the open bottom 76 of the housing 72. In the embodiment shown, the open bottom 76 is internally threaded and the medication cup 92 is externally threaded. When the bottom cup is attached, a closed chamber is formed, with the exception of the opening end 82 of the tube and the open top outlet 78.

The bottom cup 92 has substantially cylindrical outer walls 94. The bottom cup 92 has a conical portion 96 extending from a base 98 that is concentric with the walls 94. At the concentric top of the conical portion 96 is an orifice 100. Extending from the conical portion 96 and in communication with the orifice 100 is a nozzle holder 102. The nozzle holder would be connected to a source of pressurized air (not shown) so that pressurized air would be delivered into the nebulizer 70. Received within the bottom medication cup 92 is a capillary cover 104 which nests on top of the conical portion of the bottom cup 92. The capillary cover 104 has an opening 106 which is aligned with the orifice 100 of the bottom cup.

During operation of the nebulizer 70, a stream of pressurized air indicated by arrow 108 flows through the orifice of the bottom cup and causes induction of the liquid medication 124 (illustrated by dashed lines) from the bottom cup through a space between the capillary cover and the conical portion. Accordingly, liquid droplets of medication will be moved at high velocity through the orifice and into the housing 72.

A target frame 110 extends from the capillary cover and is above the opening 106 in the capillary cover. A target 112 is supported by the frame 110.

The target 112, thus, provides a target against which liquid droplets and pressurized air will move at high velocity. The stream of pressurized air and liquid droplets exiting from the opening 106 will, thus, be caused to impinge against the target 112. After striking the target 112, the mixture of liquid droplets and air will move upward and against the air inlet tube 80. It will be observed that the air inlet tube 80 itself thus serves as a baffle mechanism for the liquid particles.

Accurate skirts 114 extend radially outward from the air intake tube 80. The end of the skirts may touch and rest against the target frame 110.

Near the open bottom 76, the housing is an enlarged chamber 116 that is axially aligned with the chimney and has a larger diameter than the chimney. Ambient air from the air intake tube will traverse the housing within the intake tube and will enter the enlarged chamber 116. The air will then change direction and enter the chimney 74 as indicated by the arrows 118. Once inside the chimney, the air will pass around the horizontal air intake tube 80 and mix with the liquid droplets and pressurized air. The fine mist produced by the liquid droplets and pressurized air impinging on the target 112 is mixed and swept along with the atmospheric air. The air flow is then directed upward through the interior of the chimney 74.

Finally, the saturated mist (the droplets which are surrounded by high relative humidity) will exit the nebulizer 70 to be inhaled by the patient and is not shown from the top outlet 78 as indicated by the arrow 120.

In the typical usage, a patient will inhale through outlet 78. However, the flow through the nebulizer 70 may be reversed. In that case, the patient will inhale through inlet tube 80. Passage of the saturated mist through the circuitous route out of the tube 80 will further reduce the size of the particles. During exhaling, to prevent any secretions from the patient from entering the medication cup, the interior of the inlet tube may contain a raised shoulder 121 (seen in FIG. 2).

Returning to a consideration of the air intake tube 80, a longitudinal chamber 122 extends adjacent the chimney 74. The chamber 122 extends radially from and is in communication with the air intake tube 80. If the nebulizer 70 is accidentally tipped from the upright position in one direction, any liquid medication will flow into the chamber 122. If the nebulizer is accidentally tipped from the upright position in the opposite direction, the liquid medication will flow into the enlarged chamber 116. The foregoing arrangement and design prevents liquid medication from spilling out of the intake tube 80 or out of the chimney top outlet 78.

Figure 3:
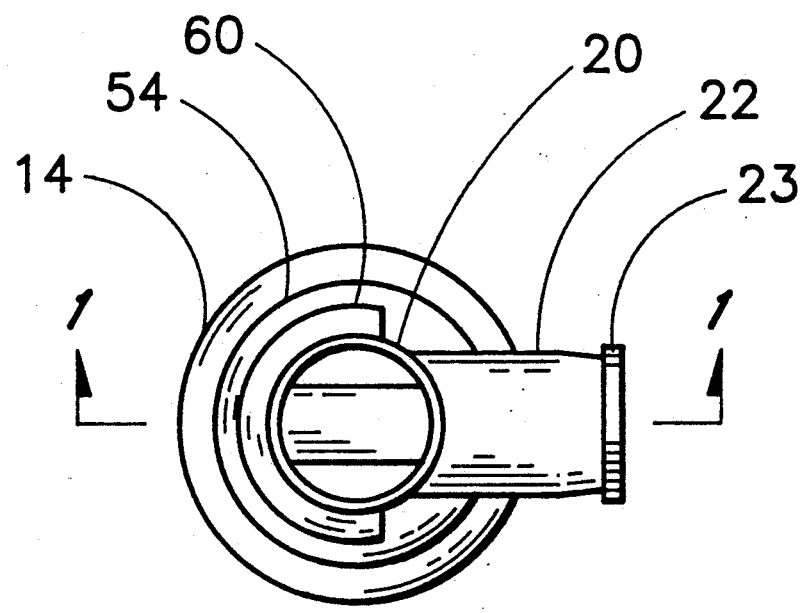
FIG. 3 is a top view of the nebulizer shown in FIG. 1.

FIG. 3 is a top view of the nebulizer 10 shown in FIG. 1. The traversal of the air inlet tube 22 across the housing 14 may be observed by viewing through the open top outlet 20. It will be appreciated that the mixture of liquid droplets, pressurized air and atmospheric air must pass around the air intake tube before passing up the chimney 16 and out of the open top outlet 20.

Figure 4:
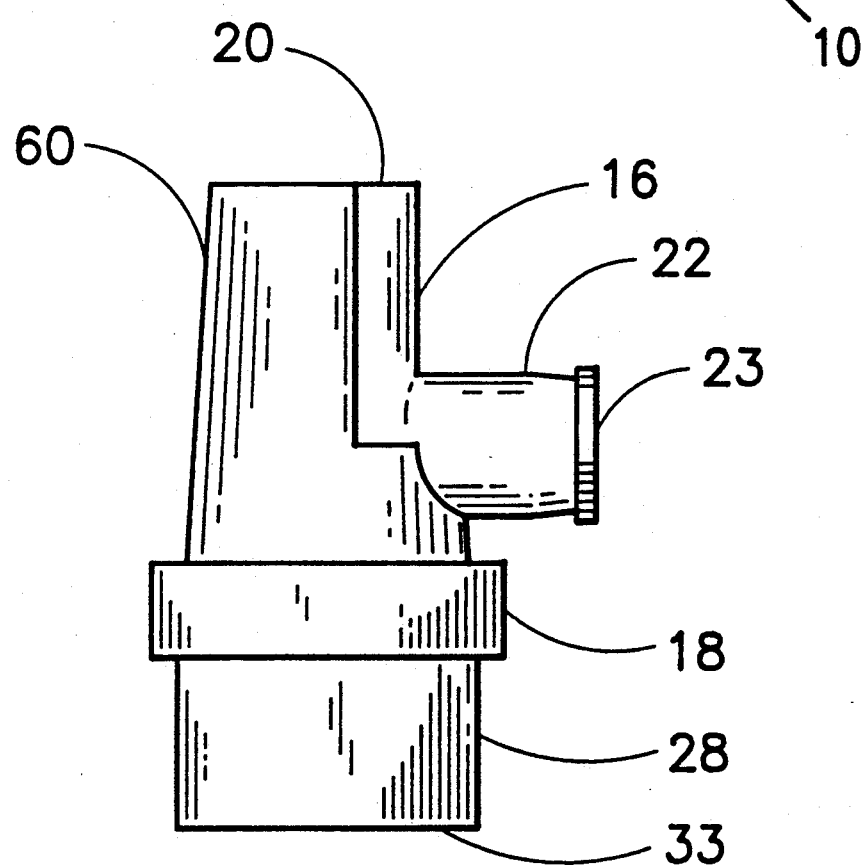
FIG. 4 is a side view of the nebulizer shown in FIG. 1.
Figure 5:
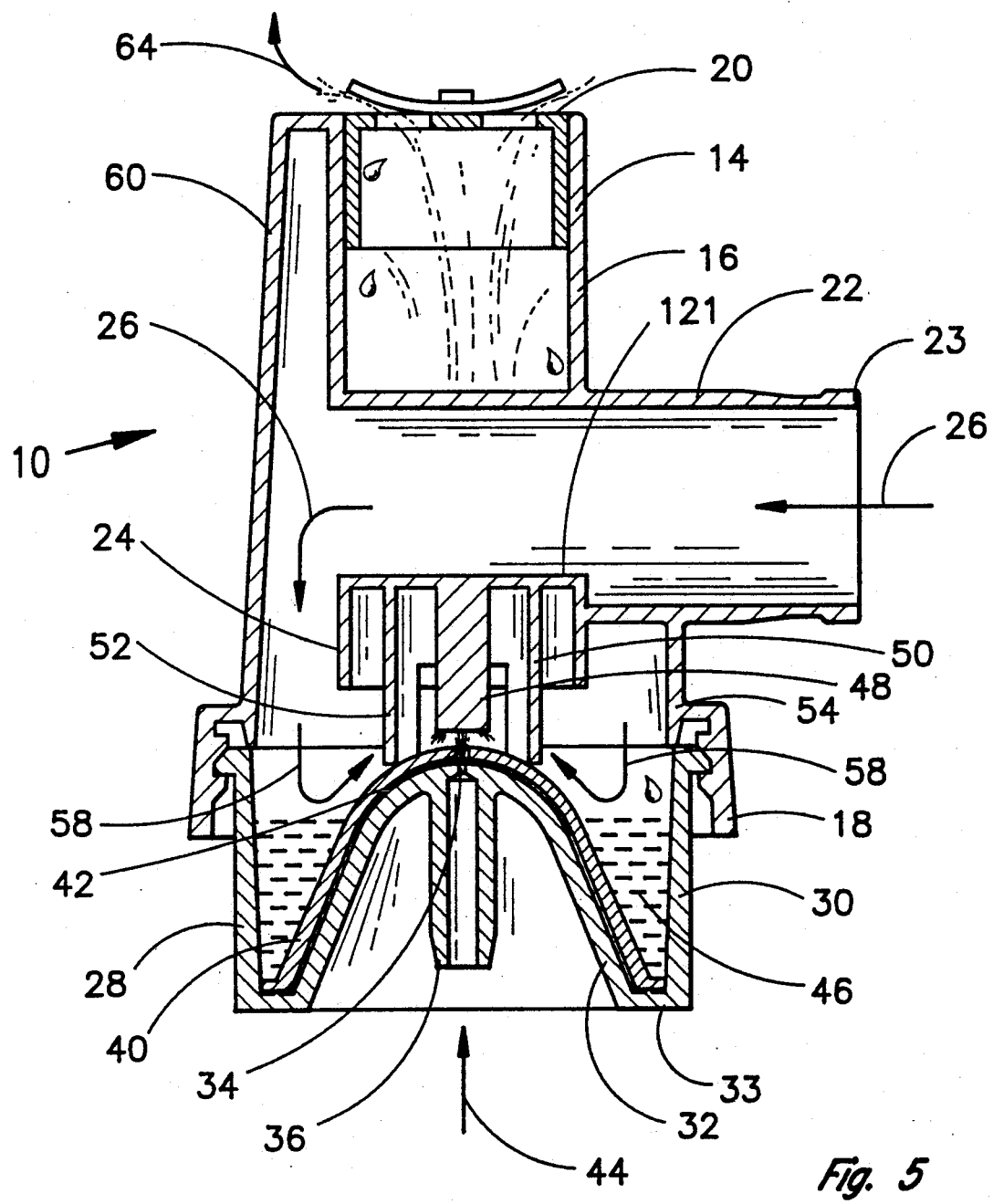
FIG. 5 is a sectional view of a nebulizer constructed in accordance with the present invention and disclosing a check-valve adjacent the open top outlet.

FIG. 4 is a side view of the nebulizer 10 shown in FIG. 1. The longitudinal chamber 60 is readily observable. If the nebulizer is tipped from the upright position or turned upside down, the liquid medication 16 in the bottom cup will flow into the longitudinal chamber. The medication will thus be prevented from spilling out of the nebulizer.

Whereas the present invention has been described in relation to the drawings attached hereto, it should be understood that other and further modifications, apart from those shown or suggested herein, may be made within the spirit and scope of this invention.

What is claimed is:

1. A nebulizer which comprises:
   (a) a bottom cup for storing liquid medication therein, said bottom cup having an opening therethrough to receive a source of pressurized air;
   (b) a substantially cylindrical housing having an open bottom removably attachable to said bottom cup, and an open top outlet;
   (c) an air inlet tube traversing said housing, said air inlet tube extending a cross the diameter of said housing perpendicular to said housing and terminating in an aperture adjacent said open bottom so that substantially all of the air entering said inlet tube upon inhalation of a patient will pass across and transversely to said housing before entering said housing adjacent said open bottom; and
   (d) a cover receivable within said bottom cup so that liquid medication may be drawn from said bottom cup by induction and form droplets, whereby said air inlet tube of said housing acts as a target for said pressurized air and said liquid droplets to impinge thereon, thereby breaking said droplets into micron-size droplets.

2. A nebulizer as set forth in claim 1 wherein said housing includes a cylindrical chamber axially aligned and in communication with said housing having a diameter larger than said housing, so that air from said air inlet tube will pass into said cylindrical chamber.

3. A nebulizer as set forth in claim 1 wherein said bottom cup is threadably received on said open bottom of said housing.

4. A nebulizer as set forth in claim 1 wherein said air inlet tube has a protrusion extending radially toward said open bottom and wherein said liquid droplets and said pressurized air will impinge on said protrusion, thereby breaking said liquid into micron-size droplets.

5. A nebulizer as set forth in claim 4 including a pair of opposed accurate skirts extending from said air inlet tube, said accurate skirts surrounding said protrusion and spaced inwardly from said housing.

6. A nebulizer as set forth in claim 5 wherein said accurate skirts rest against said cover.

7. A nebulizer as set forth in claim 1 including a spillage prevention and atomization chamber in fluid communication with said inlet tube extending longitudinally along the exterior of said housing to retain liquid medication in the event said nebulizer is tilted form a n upright position.

8. A nebulizer as set forth in claim 1 wherein said bottom cup has a conical portion extending from a base and said pressurized air opening is at a concentric top of said conical portion and wherein said cover is received over said conical portion for delivery of liquid medication by induction.

9. A nebulizer as set forth in claim 1 including removable check valve means in said housing near said open top outlet to provide secondary baffling and restrict passage of larger particles.

10. A nebulizer as set forth in claim 1 wherein said air inlet tube includes an interior raised shoulder to prevent secretions from passing to the bottom cup.

* * * * *

UNITED STATES PATENT AND TRADEMARK OFFICE
CERTIFICATE OF CORRECTION

PATENT NO. : 5,209,225
DATED : 05/11/93
INVENTOR(S) : Joseph G. Glenn and Craig A. Thompson It is certified that error appears in the above-identified patent and that said Letters Patent is hereby corrected as shown below:

Please add Craig Thompson as co-inventor;

Column 5, line 7, after "FIG." insert --5--;

Column 7, line 29, delete "a cross" and insert --across--;

Column 8, Claim 7, line 26, delete "form an" to --from an--.

Signed and Sealed this

Thirty-first Day of May, 1994

*Attest:*

BRUCE LEHMAN

*Attesting Officer*   *Commissioner of Patents and Trademarks*